(12) United States Patent
Warenius et al.

(10) Patent No.: US 6,878,526 B1
(45) Date of Patent: Apr. 12, 2005

(54) TREATING CANCER

(75) Inventors: Hilmar Meek Warenius, Wirral (GB); Laurence Anthony Seabra, Wirral (GB)

(73) Assignee: Theryte Limited, Liverpool (GB)

( * ) Notice: Subject to any disclaimer, the term of this patent is extended or adjusted under 35 U.S.C. 154(b) by 0 days.

(21) Appl. No.: 09/622,577

(22) PCT Filed: Feb. 18, 1999

(86) PCT No.: PCT/GB99/00506

§ 371 (c)(1),
(2), (4) Date: Oct. 5, 2000

(87) PCT Pub. No.: WO99/42821

PCT Pub. Date: Aug. 26, 1999

(30) Foreign Application Priority Data

| Feb. 18, 1998 | (GB) | ............................................. 9803446 |
| Feb. 18, 1998 | (GB) | ............................................. 9803447 |
| Jun. 5, 1998 | (GB) | ............................................. 9812151 |
| Jul. 3, 1998 | (GB) | ............................................. 9814545 |
| Feb. 10, 1999 | (GB) | ............................................. 9903035 |

(51) Int. Cl.$^7$ ........................................... G01N 33/574
(52) U.S. Cl. .................. 435/7.23; 436/65; 436/501
(58) Field of Search ........................... 435/7.23, 325, 435/32.1, 4, 6, 7.1, 7.21; 436/65, 501; 514/44; 424/93.21, 185.1; 530/350

(56) References Cited

PUBLICATIONS

Georgieva J, et al. J Clin Pathol Mar. 2001; 54 (3): 229–35.*
Tang L, et al. Melanoma Res Apr. 1999; 9 (2): 148–54.*
Levine AJ, et al. Nature Jun. 6, 1991; 351 (6326): 453–6.*
Rininger JA, et al. Carcinogenesis May 1997; 18 (5): 935–41.*
Darzynkiewicz Z, et al. Cytometry Sep. 1, 1996; 25 (1): 1–13.*
Gura, T, 1997, Systems for identifying drugs are often faulty, Science, vol. 278, pp. 1041–1042.*
Tockman, MS, et al, 1992, Considerations in bringing a cancer biomarker to clinical application, Cancer Research, vol. 52, Suppl., pp. 2711s–2718s.*
Gura (Science, 1997, 278: 1041–1042).*
Curti (Crit. Rev. in Oncology/Hematology, 1993, 14:29–39).*
Jain (Sci. Am., 1994, 271:58–65).*
Xiong et al (Genes Dev., 1993, vol. 7, p. 1572–83, abstract).*
Iijima et al (Int. J. Cancer, 1996, vol. 66(5):698–702, abstract).*
Ju He, et al., "CDK4 Amplification Is an Alternative Mechanism to p16 Gene Homozygous Deletion in Glioma Cell Lines", Canc. Res. 54(22):5804–5807, Nov. 1994.
H. Yamamoto, et al., "Coexpression of cdk2/cdc2 and Retinoblastoma Gene Products in Colorectal Cancer", Br. J. Canc. 71(6):1231–1236, 1995.
Hilmar M. Warenius, et al., "Cancer and the Cell Cycle", Swiss Institute for Experimental Cancer Research and American Association for Cancer Research, Lausanne Switzerland, Jan. 17–20, 1996(one page).
Ziad A. Khatib, et al., Coamplification of the CDK4 Gene and MDM2 and GLI Human Sarcomas, Cancer Research, 53(22):5535–5541, Nov. 15, 1993.

* cited by examiner

Primary Examiner—Larry R. Helms
Assistant Examiner—Stephen L. Rawlings
(74) Attorney, Agent, or Firm—Rothwell, Figg, Ernst & Manbeck p.c.

(57) ABSTRACT

Provided is a method for the diagnosis of a cancerous or pre-cancerous state in a subject, comprising testing a sample comprising cells or an extract therefrom for the co-elevation of CDK1 and CDK4. Also provided is a kit for the diagnosis of a cancerous or pre-cancerous state in a subject, comprising: (i) a means for testing for the elevation of CDK1; and (ii) a means for testing for the elevation of CDK4.

9 Claims, 4 Drawing Sheets

TREATING CANCER

The present application concerns methods of diagnosing cancer. In particular the application concerns a method for diagnosing cancer by measuring the levels of two proteins present in suspected cancer cells.

The hallmark of cancer is a capacity for unlimited, autonomous cellular proliferation. The discovery of a means of selective inhibition of proliferation in cancer cells without concomitant damage to the proliferative capacity of normal cells, could potentially provide new ways to halt the growth of tumours irrespective of their degree of differentiation, invasion or metastasis. It is interesting to understand how cancer cells divide and whether this may differ from normal cell division. Most treatments for cancer are broadly cytotoxic, generally targeting proliferating cells. Normal tissues also proliferate, however, and so are also damaged by cytotoxic agents. Identification of cancer specific markers that permit targeting or that provide specific targets for drug development would allow the development of treatments that are more specifically toxic to tumour tissues thus reducing the debilitating effects of chemotherapy.

The effect of the expression of single genes alone on the response of human cancer cell lines to treatment with cytotoxic drugs such as CDDP has been studied in human in vitro cell lines because these present a model system relevant to the response of human cancer in the clinic. In particular, they exhibit the range of sensitivities to cytotoxic drugs and ionising radiation usually encountered in the clinic. Discoveries in human in vitro cell lines, therefore, have a strong possibility of being able to be translated into clinically usefull tests for how well cancers may be expected to respond to treatment.

The progress of cells through the cell cycle is governed by holoenzymes formed by a combination of proteins called cyclins, whose levels fluctuate throughout the cell cycle, and cyclin dependent kinases (CDKs) which become active when they join with cyclins. The cyclin/CDK complexes can be inhibited by proteins termed cyclin dependent kinase inhibitors (CDKIs) which include the protein p21 WAF1/CIP1 (p21).

The protein products of the cyclin D1 and B1 genes and their respective cyclin-dependent kinase partners CDK4 and CDK1 have been studied. Cyclin D1 and CDK4 control the progress of cells through the cell cycle checkpoint between G1 and S-phase (the phase of DNA synthesis). Cyclin B1 and CDK1 control the cell cycle checkpoint just before mitosis. The expression of cyclin D1 protein in a series of 16 human cancer cell lines has been shown to be related to their intrinsic resistance to the cytotoxic drug CDDP (Warenius et al., 1996). Cyclin D1 protein levels, however, showed no relationship with radiosensitivity, another treatment modality. The relationship between cyclin D1 and CDDP resistance is not, however, strong enough on its own to provide the basis of clinically useful predictive assays.

The present invention aims to solve the problems associated with the above prior art and to provide an improved method for the diagnosis of cancer.

Accordingly, this invention describes methods of diagnosing a cancerous state by contemporaneously measuring the properties of two or more cancer-related genes. This application deals with measuring the levels of the protein product of the CDK1 gene and the protein product of the CDK4 gene, preferably whilst also determining the mutational status of p53.

Specifically this invention provides a method for the diagnosis of a cancerous or pre-cancerous state in a subject, comprising testing a sample comprising cells or an extract therefrom for the co-elevation of CDK1 and CDK4.

The co-elevation of CDK1 and CDK4 can be either elevation in their expression or their protein levels. The elevation of expression of CDK1 and CDK4, or the elevation of CDK1 and CDK4 protein levels can be measured by any appropriate method, e.g. Western blotting. The point at which it is considered that the level is elevated or that the expression is elevated (or over-expression) is clear to the skilled person in this field, according to general teaching from the literature regarding usual levels of CDK1 and CDK4 in human cell lines (see Cancer Research, 1994, Nov. 15; 54(22), 5804–7; Cancer Research, 1993, Nov. 15; 53(22), 5535–41; and British Journal of Cancer, 1995, June; 71(6), 1231–6). This point can be determined according to the judgement of the individual carrying out the present method, depending on the particular cells and patient involved.

The invention also provides a kit for the diagnosis of a cancerous or pre-cancerous state in a subject, comprising:

(i) a means for testing for the elevation of CDK1; and (ii) a means for testing for the elevation of CDK4.

The invention also provides a kit for the diagnosis of a cancerous or pre-cancerous state in a subject, comprising:

(a) a means for testing for the elevation of CDK1;

(b) a means for testing for the elevation of CDK4;

(c) a means for identifying mutant p53 cells; and (d) a means against which the elevation and the levels of CDK1 and CDK4 can be compared.

Furthermore this invention provides a novel, complex, target for drug screening which might lead to drugs that are more specifically toxic to cancer tissues with the features disclosed in this invention.

This invention specifically deals with measuring the levels of CDK1 protein and levels of CDK4 protein, in cells. The p53 mutational status of the cells has preferably been identified, e.g. by DNA sequencing. High levels of CDK1 and CDK4 are found in human cancer cells, especially those bearing p53 mutations.

Modulation of the Relationship Between CDK1 and CDK4 in p53 Mutant Human Cells

The above are unusual findings that do not fit with what is widely known about CDKs at the present time. Disruption of the CDK1/CDK4 relationship in p53 mutant cells can be identified as a new target for anticancer therapy. In addition because both the CDK1/CDK4 co-elevation and p53 mutation are confined to cancer cells and appear to be interrelated, they form in combination a complex target that is likely to prove the most specific one for cancer therapy that has so far been discovered.

The invention will now be described in further detail by way of example only, with reference to the accompanying drawings, in which.

Figure 1:
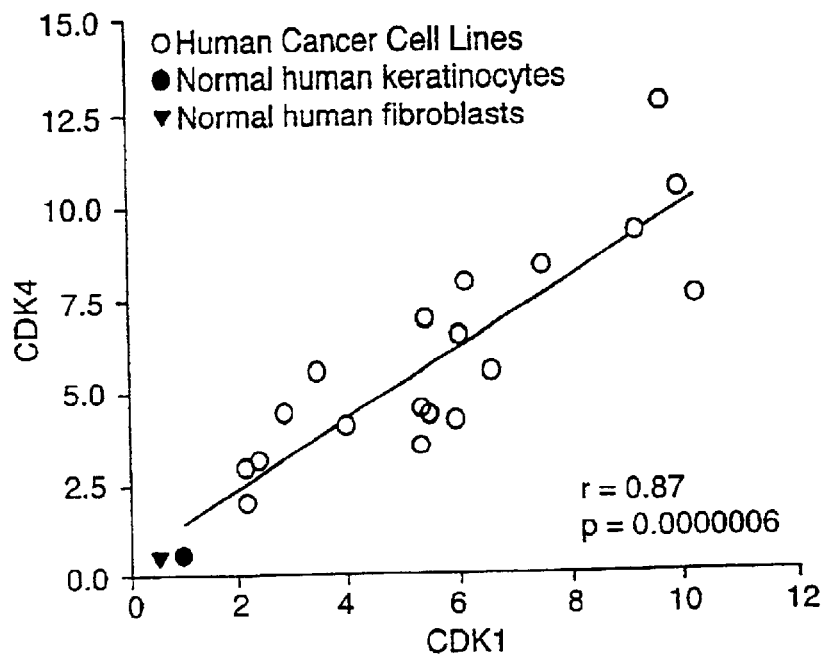
FIG. 1 shows the correlation between CDK1 and CDK4 levels in human cancer cell lines as well as the corresponding levels in normal cells such as human keratinocytes and human fibroblasts.
Figure 2:
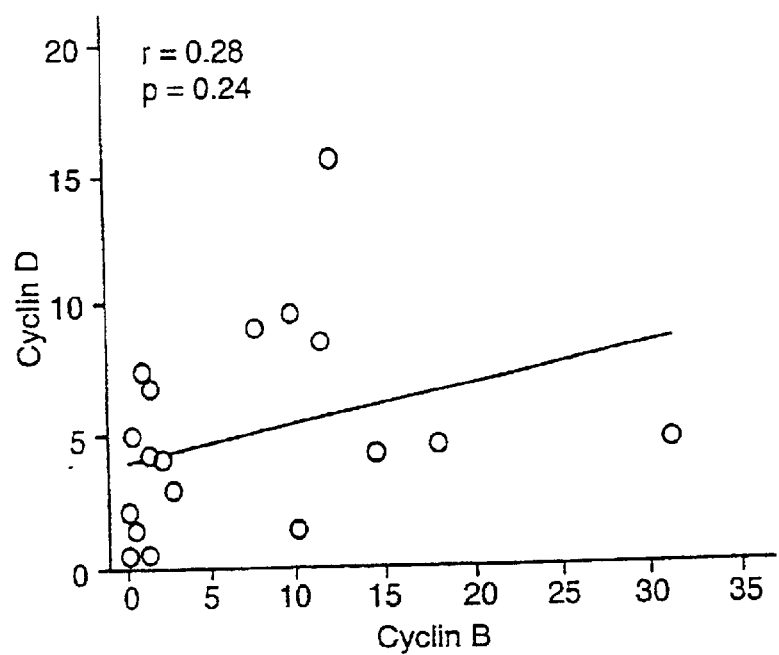
FIG. 2 shows the relative lack of correlation between cyclin D and cyclin B (the respective partners of CDK4 and CDK1) levels in human cancer cell lines.

A Dual Parameter Test for Cancer using CDK1 and CDK4 Protein Expression

A clinical test for cancer is provided based on the measurement of CDK1 protein expression levels, CDK4 protein expression levels and detection of mutations in the p53 gene. In a research environment CDK protein levels are typically measured by Western blotting or by immunocytochemistry but for diagnostic purposes cheaper and more rapid methods are more preferable.

The determination of the mutational status of p53 can be effected by sequencing the genomic locus bearing the gene from the patient or by sequencing the expressed mRNA after conversion to cDNA. Various nucleic acid sequencing methodologies are available at present, all of which are appropriate for use with this diagnostic assay. The most widely used method would be based on incorporation of terminating nucleotides into polymerase generated copies of a template, using the method of Sanger et al, 1977. Many alternatives have arisen recently including adaptor sequencing (PCT/US95/12678), ligation based sequencing (PCT/US96/05245), sequencing by hybridisation (A. D. Mirzabekov, TIBTech 12: 27–32, 1994) to list a few. Various methods for testing for specific mutations exist and are well known in the art, such as the TaqMan® (PCR) assay, oligonucleotide ligase assays, single strand conformational polymorphisms and assays based on hybridisation of template nucleic acids to oligonucleotide arrays.

Because CDK1 and CDK4 are not under direct transcriptional control, it is unlikely that mRNA levels for CDK1 and CDK4 will follow the same pattern as their proteins. This means that determination of the mRNA levels of these genes is not sufficient for the purposes of this test.

Immunocytochemistry

In a preferred embodiment of this invention, CDK1 and CDK4 protein levels could be measured by immunocytochemistry using confocal laser fluorescence microscopy to detect antibody binding. Preferably a scanning system would be used such as those described in PCT/US91/09217, PCT/NL/00081 and PCT/US95/01886. An antibody against CDK1 (such as the Mouse monoclonal sc-54 (SANTA CRUZ BIOTECHNOLOGY) would be labelled with one dye, an antibody against CDK4 (such as the purified rabbit polyclonal sc-260 (SANTA CRUZ BIOTECHNOLOGY) would be labelled with a second dye whilst a third DNA binding dye could be used to select for aneuploid cells. DNA binding dyes such as 2'-[4-hydroxyphenyl]-5-[4-methyl-1-piperazinyl]-2-5'-bi-1H-benzimidazole (HOECHST 33258) which binds AT-rich DNA, or $3^B$-O-(4-O-acetyl-2,6-dideoxy-3-C-methyl-$\alpha$-L-arabino hexapyranosyl)-7-methylolivomycin D (Chromomycin $A_3$) which binds GC-rich DNA, would be appropriate. The intensity of fluorescence from these dyes would provide an indication of the expression level of genes. A diagnostic test may comprise the steps of:

Extracting a biopsy of the tumour from a patient.

Optionally micro-dissecting that material to separate normal tissue from tumour material.

Preparing the biopsy material for microscopy which includes the steps of:

Labelling the biopsy material with the above fluorescently labelled antibody probes against CDK1 and CDK4. The biopsy material may also optionally be labelled with antibody probes against p53 mutant proteins and with a DNA binding dye.

Separating the labelled cells from unbound labelled probes.

Placing the labelled biopsy material in a scanning confocal microscope to count cells that:

Over-express or show elevation of CDK1, i.e. are labelled with at least a threshold quantity of antibody against CDK1.

Over-express or show elevation of CDK4, i.e. are labelled with at least the threshold quantity of antibody against CDK4.

Optionally, express mutant forms of p53, i.e. are labelled with at least the threshold quantity of antibodies against p53 mutants. Alternatively, p53 mutational status might be determined by analysis of the mRNA or genomic DNA as discussed above.

Optionally, have chromosomal amplifications as detected by the intensity of fluorescence from DNA binding fluorescent dyes.

Fluorescence Activated Cell Sorting

One embodiment of the diagnostic test could exploit Fluorescence Activated Cell Sorting (FACS). A FACS instrument separates cells in a suspension in a manner dependant on the cells being labelled with a fluorescent marker. A typical FACS device operates as follows. Cells in a suspension travelling in single file are passed through a vibrating nozzle which causes the formation of droplets containing a single cell or none at all. The droplets pass through a laser beam. Fluorescence from each individual cell in its droplet, excited by a laser, is measured. After the detector the stream of cells in suspension pass through an electrostatic collar which gives the droplets a surface charge. The cell carrying droplets are given a positive or negative charge. If the drop contains a cell that fluoresces with an intensity above a particular threshold, the drop gets a charge of one polarity. Unlabelled cells get a charge of the opposite polarity. The charged droplets are then deflected by an electric field and, depending on their surface charge, are directed into separate containers and are counted. Droplets that contain more than one cell scatter light more than individual cells. This is readily detected and so these are left uncharged and enter a third disposal container.

Multi-channel fluorescent detection devices have been constructed that can separate cells on the basis of labelling with multiple different fluorescent labels. These have multiple lasers which can excite fluorescence at different frequencies and the detector will detect different emission frequencies. Using this technique a test could be carried out using a multi parameter array on a flow cytometer without the need for sorting. A three label system would be appropriate for this test. An antibody against CDK1 would be labelled with one dye, an antibody against CDK4 would be labelled with a second dye whilst a third, DNA binding dye can be used to select for aneuploid cells. DNA binding dyes such as HOECHST 33258 (2'-[4-hydroxyphenyl]-5-[4-methyl-1-piperazinyl]-2-5'-bi-1H-benzimidazole) which binds AT-rich DNA, or $3^B$-O-(4-O-acetyl-2,6-dideoxy-3-C-methyl-$\alpha$-L-arabino hexapyranosyl)-7-methylolivomycin D (Chromomycin $A_3$) which binds GC-rich DNA, are appropriate. Additionally, a number of antibodies are commercially available which can detect some of the mutant forms of p53. Antibodies such as these may be labelled with a fourth dye. The intensity of fluorescence from these dyes gives an indication of the expression levels of the proteins and indicates the chromosomal status of labelled cells passing the detector. A minimum level of fluorescence intensity from each dye present in an individual cell may be required to classify a cell as being cancerous. At present not all mutant forms of p53 can be detected using antibodies, although antibodies exist against a number of known mutant forms of the p53 protein. A diagnostic test may comprise the steps of:

Extracting a biopsy of the tumour from a patient.

Optionally micro-dissecting that material to separate normal tissue from tumour material.

Disrupting intracellular adhesion to form a single cell suspension.

Labelling the suspended cells with the above fluorescently labelled probes against CDK1 and CDK4. The biopsy material may also, optionally be labelled with antibody probes against p53 mutant proteins and with a DNA binding dye.

Separating the labelled cells from unbound labelled probes.

Passing the labelled cell suspension through a FACS device to count cells that:

Over-express or show elevation of CDK1, i.e. are labelled with at least a threshold quantity of antibody against CDK1.

Over-express or show elevation of CDK4, i.e. are labelled with at least the threshold quantity of antibody against CDK4.

Optionally, express mutant forms of p53, i.e. are labelled with at least the threshold quantity of antibodies against p53 mutants. Alternatively, p53 mutational status may be determined by analysis of the mRNA or genomic DNA as discussed above.

Optionally, have chromosomal amplifications as detected by the intensity of fluorescence from DNA binding fluorescent dyes.

EXAMPLE 1

Human in vitro cell lines of different histological origin which exhibit a range of intrinsic sensitivity to cytotoxic drugs as measured by clonogenic cell survival assays, have been shown to provide appropriate models of clinical tumours, particularly in their responses to chemotherapy. In particular, these cell lines exhibit the range of sensitivities to cytotoxic drugs and ionising radiation usually encountered in the clinic. These human in vitro cancer cell lines are now widely recognised as relevant models for the clinical response of tumours to chemotherapy. It is therefore possible to identify genes from these cancer models whose expression and/or mutational status is tumour specific, which are also features of real clinical tumours. Discoveries in human in vitro cell lines, such as those leading to this invention, therefore, have a strong possibility of being able to be translated into meaningful targets for drug discovery programs.

A body of work has been carried out analysing the expression of a number of genes that have been implicated in the cancer disease process. In contrast to any of the other genes controlling cell division that were examined, CDK1 and CDK4 appeared to be consistently co-elevated in a large series of human cancer cell lines and extracts from clinical colon cancer. Without being limited by theory, it is hypothesised that for cancer cells to be able to continue to divide successfully it may be necessary a) for CDK1 and CDK4 to retain their normal functions and b) for the elevated levels of these two proteins in human cancer to be related in some way, the mechanism of which is unclear.

To investigate the above hypothesis DNA sequencing was carried out on all the exons of both CDK1 and CDK4 in the 20 human cell lines in which a strong relationship between the expression of the two proteins was detected. There were no mutations in the exons of the CDK1 and CDK4 genes in the 20 human in vitro cell lines that were sequenced. This finding is very surprising, because cancer cells are well known to progressively accumulate mutations in the critical genes controlling cell division and this is held by many scientific practitioners in this field to be most marked in human in vitro cell lines such as those investigated.

MATERIALS AND METHODS

Cell Lines and Clonogenic Cell Survival Assays

The growth characteristics clonogenic assay procedures of the human in vitro cell lines used in this analysis have already been reported (Warenius et al 1994). The cell lines are listed, with their histological classification in Table 1. All are well established; many having been growing in vitro for several years. Cell lines were either donations or purchased by our laboratories. On receipt all were grown for 5 passages to provide sufficient cells for batch storage in liquid nitrogen. During this period contamination was excluded by at least one passage in antibiotic free medium and mycoplasma testing was carried out on all lines. For clonogenic assays, cells were taken from a designated primary liquid nitrogen batch and grown for 3–6 passages until there were sufficient well-growing cells. Further batches from these cells were frozen in liquid nitrogen. Cells were routinely maintained in DMEM medium except RT112 and H322, which were grown in RPMI1640 and MGHU-1 which were grown in Ham's F12 medium. All lines were supplemented with 10% heat-inactivated foetal calf serum (HIFCS).

TABLE 1

| | Cell Line | p53 mutational status | | |
|---|---|---|---|---|
| | | cDNA sequence | Amino-acid change | p53 protein |
| I407 | Embryonic intest. epith. | Normal | none | Wild-type |
| HEP 2 | Squamous carcin. larynx | Normal | none | Wild-type |
| MGHU 1 | Transit. carcinoma bladder | Normal | none | Wild-type |
| HRT 18 | Adenocarcinoma rectum | Normal | none | Wild-type |
| 2780 | Ovarian carcinoma | Normal | none | Wild-type |
| OAW 42 | Ovarian carcinoma | CGA-CGG codon 213 | none | Wild-type |
| HT 29/5 | Adenocarcinoma colon | CGT-CAT codon 273 | Arg-His | Mutant |
| COLO 320 | Adenocarcinoma colon | CGG-TGG codon 245 | Arg-Tryp | Mutant |
| H 322 | Small cell carcinoma lung | CGG-TGG codon 245 | Arg-Tryp | Mutant |
| H 417 | Small cell carcinoma lung | GAG-TAG codon 298 | Glu-Stop | Truncated |
| RPMI 7951 | Melanoma | TCA-TTA codon 166 | Ser-Stop | Truncated |
| RT 112 | Transit. carcinoma bladder | CCG-CAG codon 248 | Arg-Gly | Mutant |

TABLE 1-continued p53 mutational status

| | Cell Line | cDNA sequence | Amino-acid change | p53 protein |
|---|---|---|---|---|
| MOR | Adenocarcinoma lung | C deletion codon 152 | Frameshift 178aa | Truncated |
| MEL 2 | Melanoma | CGC-AGC codon 245 | Gly-Ser | Mutant |

Identification of Mutations in the p53 Gene by PCR and DNA Sequencing

Material for PCR and DNA sequencing of p53 was obtained from the same liquid nitrogen batches used to provide cells for clonogenic cell survival data. Cells were grown for up to three passages prior to being subjected to the following procedures:

Nucleic Acid Isolation

RNA and genomic DNA were prepared from the cell lines described here by the guanidinium isothiocyanate CsCl gradient method (Chirgwin et al, 1979, Barraclough et al, 1987). Briefly, the cells were collected in ice-cold phosphate-buffered saline (PBS) and homogenised in guanidinium isothiocyanate buffer (4M guanidinium isothiocyanate, 50 mM Tris pH 7.5, 25 mM EDTA pH 8.0, 0.5% (w/v) sodium lauryl sarcosine and 8% (v/v) 2-mercaptoethanol added just prior to use. The homogenate was cleared by centrifugation at 8,000 rpm for 10 mins at 4° C. (SS34 rotor, Sorvall® RC-5B centrifuge) and the RNA pelleted by centrifugation of the homogenate through a cushion of 5.7M caesium chloride/0.1M EDTA at 32,000 rpm for 20 hr at 20° C. (TST 41.14 rotor, Kontron® Centrikon™ T20 60 ultracentrifuge). The pellet of RNA was redissolved in 0.1% (w/v) SDS and precipitated with ethanol overnight at −20° C. before quantitation.

Polymerase Chain Reaction, cDNA Synthesis and Nucleotide Sequencing

PCR (for exons 2–8 and for exons 9–11) was performed on DNA and RNA extracted from the human carcinoma cell lines. Each exon was then examined by DNA sequencing. PCR Primers were designed flanking each exon and synthesised on an Applied Biosystems 381A DNA synthesiser. Each exon was amplified separately with the exceptions of exons 2 and 3 which were amplified as a unit, and exons 9, 10 and 11 which were amplified together by reverse transcription polymerase chain reaction (RTPCR). The following primers were used:

Exon 2/3 sense 5'-CCC ACT TTT CCT CTT GCA GC-3' (SEQ ID NO:1)
Exon 2/3 antisense 5'-AGC CCA ACC CTT GTC CTT AC-3' (SEQ ID NO:2)
Exon 4 sense 5'-CTG CTC TTT TCA CCC ATC TA-3' (SEQ ID NO:3)
Exon 4 antisense 5'-GCA TTG AAG TCT CAT GGA AG-3' (SEQ ID NO:4)
Exon 5 sense 5'-TGT TCA CTT GTG CCC TGA CT-3' (SEQ ID NO:5)
Exon 5 antisense 5'-CAG CCC TGT CGT CTC TCC AG-3' (SEQ ID NO:6)
Exon 6 sense 5'-GCC TCT GAT TCC TCA CTG AT-3' (SEQ ID NO:7)
Exon 6 antisense 5'-TTA ACC CCT CCT CCC AGA GA-3' (SEQ ID NO:8)
Exon 7 sense 5'-ACT GGC CTC ATC TTG GGC CT-3' (SEQ ID NO:9)
Exon 7 antisense 5'-TGT GCA GGG TGG CAA GTG GC-3' (SEQ ID NO:10)
Exon 8 sense 5'-T ATC CTG AGT AGT GG-3' (SEQ ID NO:11)
Exon 8 antisense 5'-T GCT TGC TTA CCT CG-3' (SEQ ID NO:12)
Exon 9/10/11 sense 5'-AGA AAG GGG AGC CTC ACC AC-3' (SEQ ID NO:13)
Exon 9/10/11 antisense 5'-CTG ACG CAC ACC TAT TGC AA-3' (SEQ ID NO:14)

Genomic DNA was digested with EcoR1 and precipitated with ethanol and resuspended in 50 μl of water (Sigma) before being subjected to PCR amplification. The DNA (1 μg) was amplified in 50 μl PCR reactions containing 20 pmoles of each primer. A 'hot start' PCR protocol was used with the dNTP's and Taq enzyme initially separated from the rest of the reaction components on a wax cushion. The reactions were placed in a pre-heated PCR block at 95° C. for 2 minutes before undergoing thirty cycles of denaturation (30s at 95° C.), annealing (30s at 60° C. for exons 2–3, 4 and 6; 65° C. for exons 5 and 8; 67° C. for exon 7; and 68° C. for exon 9–11) and extension (1 min at 72° C.). The PCR products were checked on a 0.8% (w/v) agarose gel before being purified using a Wizard minicolumn (Promega®), and used directly in sequencing reactions.

cDNA Synthesis and RTPCR

Complementary DNA was synthesised from approximately 5 μg of total RNA using oligo (dT) as a primer. Total RNA (5 μg), human placental ribonuclease inhibitor (HPR1) 20U and 1 μg oligo (dT) were heated at 70° C. for 10 minutes, chilled on ice, added to 1× first strand buffer (50 mM Tris-HCl, pH 8.3, 75 mM potassium chloride and 3 mM magnesium chloride), 0.01M DTT, dNTPs (0.5 mM for each deoxyribonucleoside triphosphate), 400U of Superscript Reverse Transcriptase (Gibco®) and incubated at 37° C. for 1 hour. PCR for exons 9 to 11 was carried out using 5 μl of the above incubation in a 50 μl of PCR reaction as described in the previous section.

Nucleotide Sequencing

Sequencing primers (10 pmoles) were radioactively labelled at their 5' ends with $^{32}$P-ATP (45 μCi) at 37° C. for 30 min in a reaction containing T4 Polynucleotide Kinase (PNK) (9.7U, Pharmacia™) and 1× T4 PNK buffer (10 mM Tris-acetate, 10 mM magnesium acetate and 50 mM potassium acetate). The primers used were identical to those employed in the PCR reactions except for exon 5 for which a separate sense sequencing primer was designed as follows: 5'-TAC TCC CCT GCC CTC-3' (SEQ ID NO:15). Sequencing was carried out by the dideoxynucleotide enzymatic method (Sanger et al, 1977), using the fmol DNA Sequencing System (Promega®). Any putative sequence mutations identified were confirmed by additional sequencing of the exon in the antisense direction as well as by carrying out a repeat PCR and sequencing of the cell line.

RESULTS

Mutations were found in mRNA expressed from the p53 gene in a number of cell lines (see Table 1). The mutations identified in the cell lines described here were in exons 5–8 which are known to contain the majority of p53 mutations (Hollstein et al, 1991). All these mutations have been previously described apart from the nonsense mutation identified in codon 166 of the RPMI7951 line. This along with the G to T transversion in codon 298 of H417 did not lie within the most highly conserved region of the p53 gene. In the OAW42 ovarian carcinoma cell line the single base missense mutation from CGA to CGG was silent, so that the mutant triplet still coded for the same amino acid (Arg) as is present in wild-type p53 (wtp53) protein. A normal p53 protein was thus expressed in half of the cell lines. The mRNA of the other half of the cell lines coded for abnormal p53 protein. RPMI7951 and H417 possessed stop mutations resulting in 165 and 297 amino acid truncated proteins respectively. COLO320 and H322 independently exhibited a missense G:C to A:T mutation at the same site resulting in an amino-acid substitution from Arg to Tryp. RT112 and HT29/5 also had mutations coding for changes in Arg (to Gly and His respectively). COLO320, H322 and RT112 were homozygous for p53 mutations. The other mutant lines showed evidence of retention of heterozygosity. HT29/5 and RPMI7951 both expressed small amounts of wild-type p53 mRNA though H417 expressed relatively high levels.

Western Blotting for CDK1 and CDK4

Two independent Western blottings with .lysates for each cell line loaded in pairs on each gel were carried out. $10^7$ cells were grown in 162 $cm^2$ tissue culture flasks (Costar® Ltd., High Wycombe, Bucks until they were pre-confluent but still growing exponentially. Cells were then removed by trypsinisation, resuspended in complete medium +10% FCS and washed 3 times by serial centrifugation and resuspension in PAS without serum. $1-3 \times 10^8$ viable cells were then pelleted by centrifugation and resuspended at $3 \times 10^7$ cells per ml of lysate buffer (Stock solution: 10% SDS 10 ml., 0.5M Tris pH 6.8, glycerol 10 ml., Double distilled water 62 ml. To 10 ml. of stock solution were added 100 ml of 10 mM Leupeptin +10 ml 100 mM PMSF). Protein estimations were performed and the final concentration of the lysates adjusted to 300 mg total cellular protein per 100 ml. To measure CDK1 and CDK4 proteins, 150 µg of total cellular protein in 50 µl of lysate buffer was added per lane well to a 7.5% Laemmli separating gel and electrophoresis carried out at 16° C. using 60V over 16 hours and a constant current of 500 mA. Blots were transferred to nitrocellulose at 22° C. over 16 hours using a semi-dry blotting apparatus (Bio-Rad®, Richmond, Calif.). To determine CDK1 protein expression levels the blot was incubated with the sc-054 mouse monoclonal antibody to human CDK1 (SANTA CRUZ BIOTECHNOLOGY) and then incubated with rabbit anti-mouse conjugated antibodies (Dako™ UK) at ⅟1000 and developed in alkaline phosphatase buffer containing Nitroblue Tetrazolium and 5-Bromo-4-Chloro-3-Indoyl Phosphate, (Sigma®, Poole, Dorset, UK) (50 mg/ml in dimethylformamide). To determine CDK4 protein expression levels the blot was incubated with the sc-260 rabbit Poly-clonal antibody to human CDK4 (SANTA CRUZ BIOTECHNOLOGY) and then incubated with rabbit anti-mouse conjugated antibodies (Dako™ UK) at ⅟1000 and developed in alkaline phosphatase buffer containing Nitroblue Tetrazolium and 5-Bromo-4-Chloro-3-Indoyl Phosphate, (Sigma®, Poole, Dorset, UK) (50 mg/ml in dimethylformamide).

Quantitation of the protein product of the CDK1 and CDK4 genes was carried out by measurement of optical density on a Schimadzu scanning densitometer with tungsten light and expressed as O.D. units per 150 µg of total cellular protein. Titration curves obtained by loading different amounts of total cellular protein have previously shown that linear relationships for optical density (O.D.) could be obtained over the range found for CDK1 and CDK4 protein across the cell lines. In order to compare different CDK1 and CDK4 protein levels between the cell lines, the mean O.D. value for all the lines was calculated and the relative O.D. for CDK1 and CDK4 protein in each individual cell line was normalised to the mean O.D. and multiplied by an arbitrary value of 5.0.

The cell lines investigated are shown in Table 2 below.

TABLE 2

| Cell Line | Histology |
| --- | --- |
| 2780 | Ovarian carcinoma |
| A431 | Squamous carcinoma vulva |
| A549 | Adenocarcinoma lung |
| AT5BIVA | Ataxia telangiectasia transformed fibroblast |
| COR L23 | Large cell lung carcinoma |
| G361 | Melanoma |
| H322 | Small cell carcinoma lung |
| HEP2 | Squamous carcinoma larynx |
| HRT18 | Adenocarcinoma rectum |
| HT29/5 | Adenocarcinoma colon |
| HX142 | Neuroblastoma |
| HX34 | Skin melanoma |
| I407 | Embryonic intestinal epithelium |
| KB | Oral epidermoid carcinoma |
| MEL2 | Melanoma |
| MEL3 | Melanoma |
| MGHU-1 | Transit cell carcinoma bladder |
| MOR | Adenocarcinoma lung |
| OAW42 | Ovarian carcinoma |
| RT112 | Transit cell carcinoma bladder |

Figure 3:
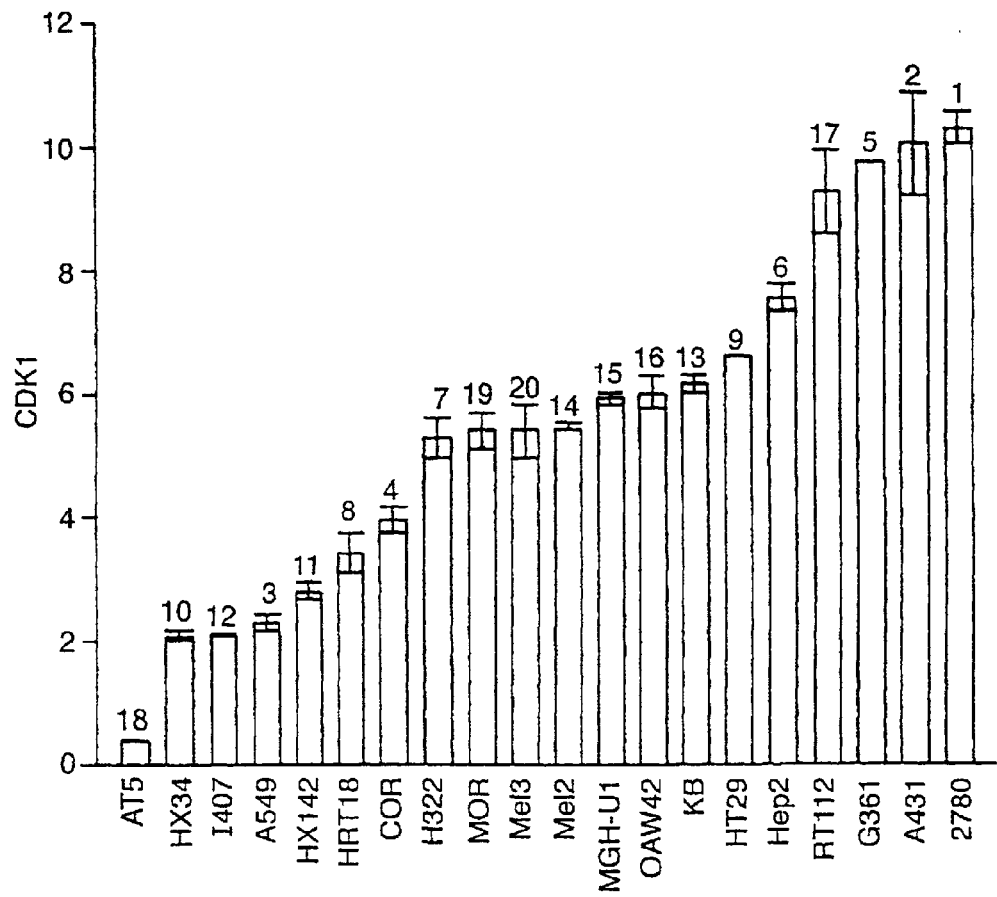
FIG. 3 shows the range of values for CDK1 levels found from several Western immunoblot runs carried out on specific human in vitro cell lines (the standard errors are also shown)
Figure 4:
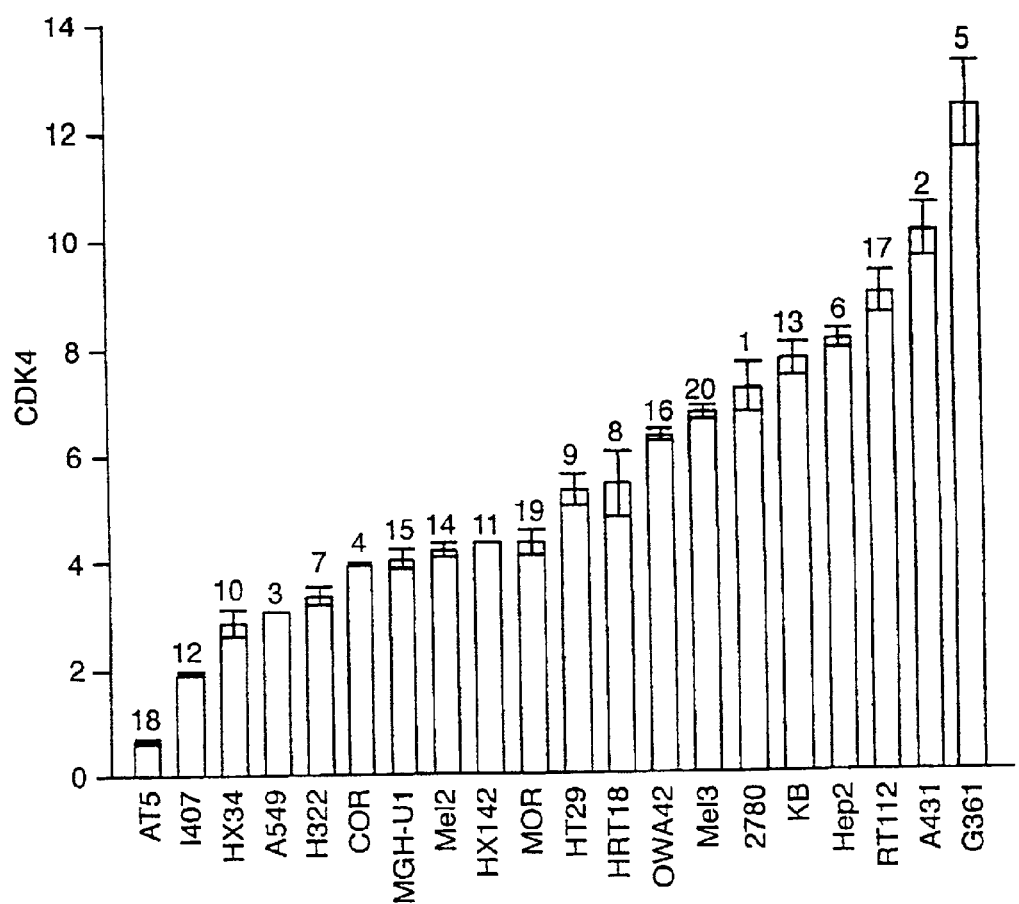
FIG. 4 shows the corresponding data to FIG. 3, obtained in respect of CDK4.

The results are shown in FIGS. 3 and 4.

Figure 5:
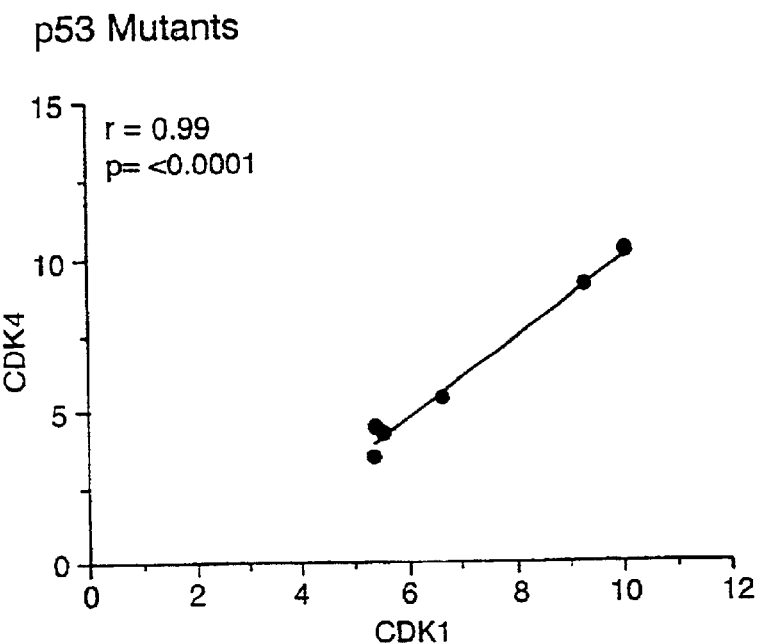
FIG. 5 shows the correlation between CDK1 and CDK4 levels in p53 mutant human cancer cell lines.
Figure 6:
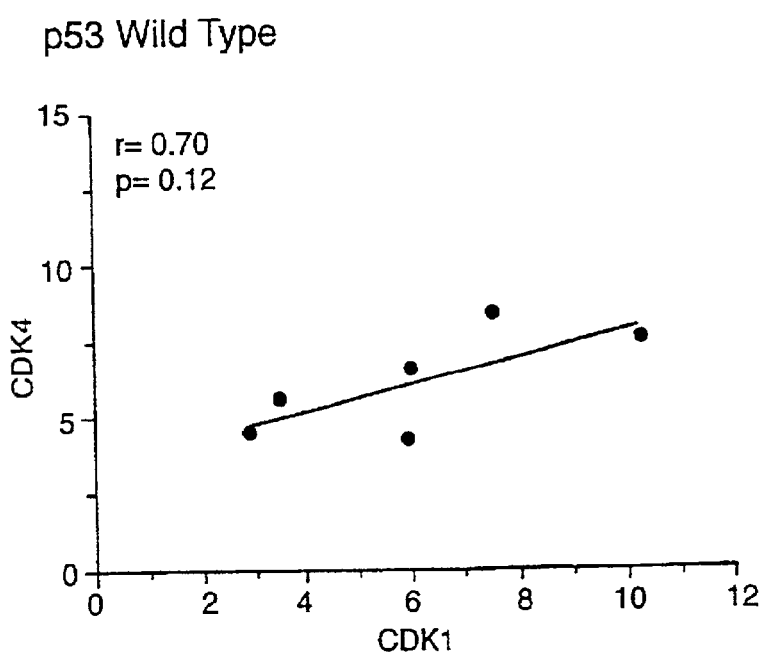
FIG. 6 shows the corresponding correlation to FIG. 5, obtained in respect of wild-type p53 human cell lines.

A strong correlation between the expression of the CDK1 and CDK4 in a series of human in vitro cancer cell lines is observed Using DNA sequencing data for p53 mutational status for a number of these lines, it is further observed that the CDK1/CDK4 relationship is particularly marked in cell lines with p53 mutations (see FIG. 5 and FIG. 6).

Also, surprisingly, the correlation seen between the protein expression for these cell lines was not seen for the relevant mRNAs. Nor was there a reciprocal correlation between the protein expression for one gene and the mRNA for the other. These results suggest that the co-elevation of CDK1 and CDK4 proteins is not at the level of transcriptional control but may be at a translational or post-translational stage. That is to say the proteins themselves are influencing each other in some way or are both influenced by an as yet unknown factor.

The findings concerning the co-relationships of CDK1 and CDK4 proteins in human in vitro cell lines and clinical colon cancers are supported by transfection studies into RAMA37, a rat normal myoepithelial cell line. Pilot studies with RAMA37 suggest that over-expression of CDK4 protein as a result of successful transfection of CDK4 under unconditional promoter control is accompanied by a concomitant elevation in the constitutive expression of CDK1.

REFERENCES

Barraclough et al, J. Cell Physiolog 131: 393–401, 1987.
Chirgwin et al, Biochemistry 18: 5294–5299, 1979.
Maskos and Southern, Nucleic Acids Research 21, 2269–2270, 1993.
Pease et al. Proc. Natl. Acad. Sci. USA. 91, 5022–5026, 1994.
Sanger et al, Proc. Natl. Acad. Sci. USA 74: 5463–5467, 1977.
Southern et al, Nucleic Acids Research 22, 1368–1373, 1994.

Warenius et al., Int. J. Cancer. 67: 224–231, 1996.
Bristow et al., Oncogene 9: 1527–1536, 1994.
Bristow et al., Radiotherapy and Oncology 40: 197–223, 1996.
P. W. G. Browning, "Proto-oncogene expression and intrinsic radiosensitivity, PhD Thesis, University of Liverpool, 1997.
Deacon et al, Radiotherapy and Oncology 2, 317–323, 1984.
Fan er al, Cancer Res. 54: 5824–5830, 1994.
Fertil & Malaise, Int. J. Radiat. Oncol. Biol. Phys. 7: 621–629, 1981.
FitzGerald et al, Radiat. Res. 122: 44–52, 1990.
Hollstein et al, Science 253: 49–53, 1991.
Iliakis et al., Cancer Res. 50: 6575–6579, 1990.
Kasid et al., Cancer Res. 49: 3396–3400, 1989.
Kastan et al, Cancer Res. 51: 6304–6311, 1991.
Kawashima et al., Int J. Cancer 61: 76–79, 1995.
Kelland et al, Radiat Res. 116: 526–538, 1988.
Lee and Bernstein, Proc. Natl. Acad. Sci. USA 90: 5742–5746, 1993.
McIlwrath et al., Cancer Res. 54: 3718–3722, 1994.
McKenna et al., Cancer Res. 50: 97–102, 1990.
McKenna et al., Radiat Res. 125: 283–287, 1991.
Nunez et al, Br. J. Cancer 71: 311–316, 1995.
Pardo et al., Radiat. Res. 140:180–185, 1994.
Pirollo et al., Int J. Radiat. Biol. 55: 783–796, 1989.
Pirollo et al., Radiat. Res. 135: 234–243, 1993.
Powell & McMillan, Int J. Rad. Oncol. Biol. Phys., 29: 1035–1040, 1994.
Radford, Int. J. Radiat Biol. 66: 557–560, 1994.
Sanger et al, Proc. Natl. Acad. Sci. USA 74: 5463–5467, 1977.
Schwartz et al., Int. J. Radiat. Biol. 59: 1314–1352, 1991.
Shimm et al., Radiat. Res. 129: 149–156, 1992.
Siles et al., Br. J. Cancer 73: 581–588, 1996.
Su & Little, Int. J. Radiat Biol. 62: 461–468, 1992.
Su & Little, Radiat. Res. 133: 73–79, 1993.
Suzuki et al., Radiat Res. 129: 157–162, 1992.
Warenius et al., Eur. J. Cancer 30, 369–375, 1994.
Warenius et al., Rad. Research 146,485–493, 1996.
Whitaker et al., Int. J. Radiat. Biol. 67: 7–18, 1995.
Xia et al., Cancer Res. 55: 12–15, 1995.
Zhen et al., Mut. Res. 346, 85–92, 1995.

What is claimed is:

1. A method for the diagnosis of a cancerous state in a subject which method comprises:
    (a) obtaining a sample of p53 mutant cells or an extract therefrom from said subject;
    (b) measuring the optical density per 150 µg total cellular protein of CDK1 and CDK4 in said sample;
    (c) normalizing the optical density of CDK1 per 150 µg total cellular protein measured in step (b) by dividing the measured optical density by the mean optical density of CDK1 per 150 µg total cellular protein and multiplying by 5;
    (d) normalizing the optical density of CDK4 per 150 µg total cellular protein measured in step (b) by dividing the measured optical density by the mean optical density of CDK4 per 150 µg total cellular protein and multiplying by 5;
    (e) determining the ratio of the normalized optical density of CDK1 to the normalized optical density of CDK4; and
    (f) diagnosing cancer when the ratio of CDK1 to CDK4 determined in step (e) is between 1.0 and 1.6, wherein said mean optical density of CDK1 per 150 µg total cellular protein is the mean optical density of CDK1 from a number of samples of p53 mutant cancer cells or an extract thereof, and wherein said mean optical density of CDK4 per 150 µg total cellular protein is the mean optical density of CDK4 from a number of samples of p53 mutant cancer cells or an extract therefrom.

2. A method according to claim 1, wherein said determination comprises contacting said sample with a labeled antibody selected from the group consisting of a CDK1 antibody and a CDK4 antibody.

3. A method according to claim 1, wherein mutant p53 cells are identified by contacting said sample with a labeled antibody against mutant p53.

4. A method according to claim 1, wherein said determination is carried out using Western blotting.

5. A method according to claim 1, wherein said sample is microdissected to separate normal tissue from tumor tissue prior to said determination.

6. A method according to claim 1, wherein normal tissue is separated from tumor tissue by contacting said sample with a DNA binding dye to label aneuploid cells and separating labeled cells from unlabeled cells.

7. A method according to claim 1, wherein said CDK1 and CDK4 are wild type CDK1 and CDK4.

8. A method according to claim 1, wherein said sample comprises cells.

9. A method according to claim 8, wherein prior to said determination, intercellular adhesion in the sample of cells is disrupted to form a single cell suspension.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 2/3 sense primer

<400> SEQUENCE: 1 cccactttc ctcttgcagc                                              20

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 2/3 antisense primer

<400> SEQUENCE: 2
agcccaaccc ttgtccttac                                             20

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 4 sense primer

<400> SEQUENCE: 3
ctgctctttt cacccatcta                                             20

<210> SEQ ID NO 4
<211> LENGTH: 20
<212> TYPE: DNA
```

```
<213> ORGANISM: Homo sapiens
<220> FEATURE:
<221> NAME/KEY: misc_feature
<222> LOCATION: ()..()
<223> OTHER INFORMATION: Cyclin D1 exon 4 antisense primer

<400> SEQUENCE: 4
gcattgaagt ctcatggaag                                              20

<210> SEQ ID NO 5
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 5 sense primer

<400> SEQUENCE: 5
tgttcacttg tgccctgact                                              20

<210> SEQ ID NO 6
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 5 antisense primer

<400> SEQUENCE: 6
cagccctgtc gtctctccag                                              20

<210> SEQ ID NO 7
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 6 sense primer

<400> SEQUENCE: 7
gcctctgatt cctcactgat                                              20

<210> SEQ ID NO 8
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 6 antisense primer

<400> SEQUENCE: 8
ttaacccctc ctcccagaga                                              20

<210> SEQ ID NO 9
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 7 sense primer

<400> SEQUENCE: 9
actggcctca tcttgggcct                                              20
```

```
<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 7 antisense primer

<400> SEQUENCE: 10
tgtgcagggt ggcaagtggc                                           20

<210> SEQ ID NO 11
<211> LENGTH: 15
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 8 sense primer

<400> SEQUENCE: 11
tatcctgagt agtgg                                                15

<210> SEQ ID NO 12
<211> LENGTH: 15
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 8 antisense primer

<400> SEQUENCE: 12
tgcttgctta cctcg                                                15

<210> SEQ ID NO 13
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 9/10/11 sense primer

<400> SEQUENCE: 13
agaaagggga gcctcaccac                                           20

<210> SEQ ID NO 14
<211> LENGTH: 20
<212> TYPE: DNA
<213> ORGANISM: Homo sapiens
<220> FEATURE:
<221> NAME/KEY: misc_feature
<222> LOCATION: ()..()
<223> OTHER INFORMATION: Cyclin D1 exon 9/10/11 antisense primer

<400> SEQUENCE: 14
ctgacgcaca cctattgcaa                                           20

<210> SEQ ID NO 15
<211> LENGTH: 15
<212> TYPE: DNA
<213> ORGANISM: Homo sapiens
<220> FEATURE:
<221> NAME/KEY: misc_feature
<222> LOCATION: ()..()
```

-continued

```
<223> OTHER INFORMATION: Cyclin D1 exon 5 sense sequencing primer

<400> SEQUENCE: 15
tactcccctg ccctc                                                    15
```